US012745913B2

(12) United States Patent
Shivpure et al.

(10) Patent No.: US 12,745,913 B2
(45) Date of Patent: Sep. 29, 2026

(54) SYSTEM AND METHOD FOR EVALUATING VASCULAR HEALTH CONDITION OF A PERSON USING THERMAL IMAGING

(71) Applicant: Aarca Research Inc., Orange, CT (US)

(72) Inventors: Sameer Raghuram Shivpure, Maharashtra (IN); Jayanthi Thiruvengadam, Tamil Nadu (IN); Gayathri Choda, Andhra Pradesh (IN)

(73) Assignee: AARCA RESEARCH INC., Orange, CT (US)

( * ) Notice: Subject to any disclaimer, the term of this patent is extended or adjusted under 35 U.S.C. 154(b) by 247 days.

(21) Appl. No.: 17/290,918

(22) PCT Filed: Aug. 14, 2020

(86) PCT No.: PCT/IB2020/057675

§ 371 (c)(1),
(2) Date: May 3, 2021

(87) PCT Pub. No.: WO2021/044240

PCT Pub. Date: Mar. 11, 2021

(65) Prior Publication Data

US 2022/0183567 A1 Jun. 16, 2022

(30) Foreign Application Priority Data

Sep. 6, 2019 (IN) ............................. 201941035981

(51) Int. Cl.
*A61B 5/01* (2006.01)
*A61B 5/02* (2006.01)
(Continued)

(52) U.S. Cl.
CPC .......... *A61B 5/015* (2013.01); *A61B 5/02028* (2013.01); *A61B 5/0261* (2013.01);
(Continued)

(58) Field of Classification Search
CPC ............................ A61B 5/015; A61B 5/02028
See application file for complete search history.

(56) References Cited

U.S. PATENT DOCUMENTS 11,903,742 B2 2/2024 Shivpure et al.
12,023,130 B2 7/2024 Shivpure et al.
(Continued)

FOREIGN PATENT DOCUMENTS

WO 2019/061418 4/2019
WO 2019/116996 6/2019
WO 2019/180065 9/2019

OTHER PUBLICATIONS

Bandyopadhyay, A. et al. "IR based intelligent image processing techniques for medical applications." 2016 SAI Computing Conference (SAI). IEEE, 2016. (Year: 2016).
(Continued)

*Primary Examiner* — Justin Xu
*Assistant Examiner* — Jonathan M Haney

(57) ABSTRACT

System and method for evaluating the vascular health condition of a subject using thermal imaging is disclosed. The system and method includes capturing passive thermal images and/or videos of at least one body part, detecting a predefined region of the body part in each frame of the captured images/videos, and segmenting one or more portions from the detected predefined region in each frame of the captured images/videos. Further a region of interest comprising blood vessels in the segmented portions in each frame of the captured images/videos is identified to extract pixel values from each frame of the captured images/videos representing biosignals. Parameters associated with the potential biomarkers of vascular functions and hemodynamics of the subject are determined based on the extracted pixel values representing biosignals. The vascular health condi-
(Continued)

tion of the subject is evaluated based on deviation of the determined parameters with respect to predetermined reference parameters.

15 Claims, 5 Drawing Sheets

(51) Int. Cl.
*A61B 5/026* (2006.01)
*G06T 7/00* (2017.01)

(52) U.S. Cl.
CPC .. *G06T 7/0016* (2013.01); *G06T 2207/10016* (2013.01); *G06T 2207/10048* (2013.01); *G06T 2207/30104* (2013.01); *G06T 2207/30201* (2013.01)

(56) References Cited

U.S. PATENT DOCUMENTS

| | | | | |
|---|---|---|---|---|
| 2003/0028114 | A1 | 2/2003 | Casscells et al. | |
| 2008/0045847 | A1* | 2/2008 | Farag | A61B 5/0082 600/500 |
| 2009/0105588 | A1 | 4/2009 | Emelianov et al. | |
| 2009/0141124 | A1 | 6/2009 | Liu et al. | |
| 2010/0172567 | A1 | 7/2010 | Prokoski | |
| 2010/0245608 | A1* | 9/2010 | Trudeau | G06T 5/92 382/172 |
| 2011/0135771 | A1 | 6/2011 | Dubey et al. | |
| 2011/0243409 | A1* | 10/2011 | Naimi | A61B 5/0091 382/128 |
| 2012/0035540 | A1 | 2/2012 | Ferren et al. | |
| 2013/0204100 | A1* | 8/2013 | Acquista | A61B 5/14539 600/509 |
| 2014/0276090 | A1 | 9/2014 | Breed | |
| 2014/0303608 | A1 | 10/2014 | Taghizadeh | |
| 2015/0118698 | A1 | 4/2015 | Michaelsen et al. | |
| 2015/0196200 | A1 | 7/2015 | Fixler et al. | |
| 2015/0206301 | A1* | 7/2015 | Mestha | G01J 5/0025 382/128 |
| 2015/0279113 | A1* | 10/2015 | Knorr | G06T 7/11 345/633 |
| 2016/0007865 | A1 | 1/2016 | Sakata et al. | |
| 2016/0117813 | A1* | 4/2016 | Gross | A61B 5/0022 600/479 |
| 2016/0157725 | A1 | 6/2016 | Munoz | |
| 2016/0180050 | A1 | 6/2016 | Holmes et al. | |
| 2017/0079533 | A1 | 3/2017 | Robinson et al. | |
| 2017/0209083 | A1 | 7/2017 | Zarandi et al. | |
| 2017/0238805 | A1 | 8/2017 | Addison et al. | |
| 2017/0238842 | A1 | 8/2017 | Jacquel et al. | |
| 2017/0245768 | A1 | 8/2017 | White et al. | |
| 2017/0367651 | A1 | 12/2017 | Tzvieli et al. | |
| 2018/0088041 | A1 | 3/2018 | Zhang et al. | |
| 2018/0098748 | A1 | 4/2018 | Kim et al. | |
| 2018/0099001 | A1 | 4/2018 | Schentag et al. | |
| 2020/0337573 | A1 | 10/2020 | Fukuda et al. | |
| 2020/0375451 | A1 | 12/2020 | Zavislan et al. | |

OTHER PUBLICATIONS

Gault, Travis R., et al. "Extraction of the superficial facial vasculature, vital signs waveforms and rates using thermal imaging." 2010 IEEE Computer Society Conference on Computer Vision and Pattern Recognition-Workshops. IEEE, 2010. (Year: 2010).

International Search Report for International Application No. PCT/IB2020/057675 mailed Oct. 26, 2020.

Kamadi, V. et al., "A computational intelligence technique for the effective diagnosis of diabetic patients using principal component analysis (PCA) and modified fuzzy SLIQ decision tree approach." Applied Soft Computing 49 (2016): 137-145. (Year: 2016).

M. Anburajan, "Changes of Skin Temperature of Parts of the Body and Serum Asymmetric Dimethylarginine (ADMA) in Type-2 Diabetes Mellitus Indian Patients," Aug. 30-Sep. 3, 2011, 33rd Annual International Conference of the IEEE EMBS, Boston, Massachusetts USA, Aug. 30-Sep. 3, 2011, pp. 6254-6259.

S.V. Mahesh Kumar, "Non-Invasive Measurement of Cholesterol Levels Using Eye Image Analysis," Oct. 19-20, 2016, vol. 14 CIC 2016 Special Issue International Journal of Computer Science and Information Security (IJCSIS), (CIC 2016), Pondicherry Engineering College, Puducherry, India Oct. 19 & 20, 2016, pp. 33-37.

Sivanandam S., et al. "Medical thermography: a diagnostic approach for type 2 diabetes based on non-contact infrared thermal imaging." Endocrine 42 (2012): 343-351 (Year: 2012).

Zhang D. et al. "Association between resting heart rate and coronary artery disease, stroke, sudden death and noncardiovascular diseases: a meta-analysis." CMAJ 188.15 (2016): E384-E392 (Year: 2016).

International Search Report for International Application No. PCT/IB2020/059244 mailed Jan. 25, 2021.

International Search Report for International Application No. PCT/IB2020/059836 mailed Feb. 8, 2021.

Shanker, N.R. et al., Non-invasive method of detection of cholesterol using image processing, International Journal of Medical Engineering and Informatics, vol. 4, No. 3, Jan. 1, 2012.

International Search Report for International Application No. PCT/IB2020/059537 mailed Jan. 26, 2021.

* cited by examiner

SYSTEM AND METHOD FOR EVALUATING VASCULAR HEALTH CONDITION OF A PERSON USING THERMAL IMAGING

CROSS REFERENCE TO RELATED APPLICATIONS

This application claims priority to International Patent Application No. PCT/IB2020/057675, filed on Aug. 14, 2020, which claims priority to Indian Patent Application number 201941035981, filed on Sep. 6, 2019. The contents of these applications are hereby incorporated by reference in their entirety.

TECHNICAL FIELD

The present disclosure relates generally to the technical field of health care systems for evaluating the health condition of a person. More particularly, the present disclosure relates to a non-contact, non-invasive system and method for evaluating the vascular health condition of a person using thermal imaging.

BACKGROUND

The background description includes information that may be useful in understanding the present invention. It is not an admission that any of the information provided herein is prior art or relevant to the presently claimed invention, or that any publication explicitly or implicitly referenced is prior art.

Chronic vascular dysfunction is associated with an increased risk of cardiovascular, peripheral vascular, cerebrovascular diseases and comorbidity conditions. The presence of metabolic disorders such as diabetes, hypertension and dyslipidemia are indications of vascular dysfunction causing early atherosclerosis and endothelial dysfunction. Vascular dysfunction includes dysfunction of arteries, microcirculation dysfunction and endothelial dysfunction. In the recent years, it was proved that the atherosclerotic process is a chronic inflammation characterized by early vascular dysfunction. Endothelial dysfunction is caused by the deficiency of nitric oxide which leads to impaired vasodilation. Endothelial dysfunction precedes atherosclerosis, metabolic syndrome and it is an independent predictor of cardiovascular events. Clinical manifestation of this pathophysiology may take several months to years and the early diagnosis of these conditions may help in early detection of related conditions before they become clinically significant.

Vascular dysfunction if not intervened in the early stages stimulates structural atherosclerosis. Efforts have been made in the past to provide solutions. For example existing diagnostic techniques for measuring the vascular health condition mostly consists of a) Imaging techniques such as Magnetic Resonance Imaging (MRI), computed tomography (CT scan), PET and ultrasound; b) Non-invasive methods such as vascular doppler, ECG, stress test; and/or c) blood tests for inflammatory markers. The invasive angiography is considered as the gold standard test for assessing the progress of the vascular dysfunction and is usually recommended only in the later stages of the condition when symptoms are prominent. Significant drawbacks of these methods are that the systems are expensive, require technical expertise to assess the condition accurately, and can only be performed on-demand or when the symptoms are already significant. Hence, these methods are often not used for pre-screening or continuous health monitoring.

Earlier literature also proposed non-contact methods for measuring hemodynamic parameters using thermal imaging. For example, in a non-patent literature (IEEE paper) titled "Contact-Free Measurement of Cardiac Pulse Based on the Analysis of Thermal Imagery" discloses a method proposed in which a line-based region along the vessel is manually selected, and the Fast Fourier transform is applied to individual points along the selected line of interest. A pulse rate is determined using the dominant frequency after filtering the noise. A method disclosed in a US patent document number U.S. Pat. No. 9,693,693B2 titled "Non-contact and passive measurement of an arterial pulse through thermal IR imaging, and analysis of thermal IR imagery" uses sequence of thermal images to detect superficial temporal arteries region and measure the heart rate, heart rate variability by applying continuous wavelet analysis on the arterial waveform. However, these cited documents have limitations in accordance with determining the health condition of a person. The disclosed methods in the cited documents are restricted only to the measurement of parameters and do not help in diagnosing the health parameters to determine any illness or chronic disorders. Each method measures only specific parameters which may not be sufficient to diagnose the health conditions. Further, the analysis was based on the thermal images captured from healthy subjects, which limits the detection of disorders since the measured parameters may differ due to the disorder.

There is, therefore, a need to provide a simple and efficient solution which can overcome the foregoing limitations in the art.

OBJECTS OF THE INVENTION

A general object of the present disclosure is to provide a simple and an efficient solution which can obviate the above mentioned changes in the art.

An object of the present disclosure is to provide an improved system for evaluating the vascular health condition of an individual.

Another object of the present disclosure is to provide an efficient system for early detection of biomarkers in individuals indicating vascular dysfunction.

Another object of the present disclosure is to provide a non-contact, non-invasive system and method to determine the hemodynamic imbalances and vascular complications of a person using thermal imaging to help in diagnosis of the health conditions.

Yet another object of the present disclosure is to provide an efficient system and method using biomarkers associated with vascular structure and functions measured from thermal imaging for assessing vascular health of an individual.

Still another object of the present disclosure is to provide a simple and cost-effective system and method which can be easily implemented for evaluating the vascular health condition as well as hemodynamic imbalances of a person to help in diagnosis of the health conditions.

SUMMARY

The aspects of the present disclosure relate to a non-contact, non-invasive system and method for determining the vascular health condition of a person. In an aspect, the disclosed system and method are based on use of thermal imaging as a non-invasive, non-contact passive method/technique for evaluating the vascular health condition of a person using biomarkers of vascular dysfunction. The disclosed system and method may be used as a diagnostic assistance tool for determining vascular health or for determining efficacy of the interventions for vascular dysfunction or other vascular disorders over time.

Vascular dysfunction in a person creates vascular complications, such as endothelial dysfunction and atherosclerosis over time. These complications impair vascular function and can cause hemodynamic changes. These vascular impairments are prominent in chronic patients and are typically associated with clinical symptoms which can be easily diagnosed using this method. The vascular dysfunction in early stages among healthy individuals is not prominent and requires measuring potential biomarkers pertaining to the variations in the vascular structure and function. The movement of the blood through the arteries is associated with the emission of heat due to inflammation and resistance of the arterial wall and is measured using the infrared thermal sensors on the major arteries that lay close to the skin surface. The structural and functional changes in the arteries caused due to endothelial dysfunction and atherosclerosis will create more resistance for the flow of blood and cause changes in hemodynamics. Since the structural abnormalities and plaque formation may be present only in some sections of the arteries, the hemodynamic parameters measured from thermal patterns for different locations will differ: These differences serve as biomarkers of vascular dysfunction.

In an aspect, the present disclosure provides a system and method for evaluating a vascular health condition of a subject, such as a human, are based on capturing any or a combination of one or more thermal images and videos of at least one body part, for example face, of the subject by a set of thermal sensors. A set of data packets associated with the captured images and/or videos is received by a processing engine comprising one or more processors and a memory storing a set of instructions executable by the one or more processors to detect a predefined region of the body part of the subject in each frame of the captured images and/or videos in response to receipt of the set of data packets, and segment one or more portions, for example a forehead or a portion of the forehead of the subject, from the detected predefined region in each frame of the captured images and/or videos. In an embodiment, a region of interest comprising one or more blood vessels in the segmented portions in each frame is identified for further extracting one or more pixel values from each frame of the captured images and/or videos based on the identified region of interest, representing a set of biosignals associated with pulsatile nature of the blood flow.

In another embodiment, one or more parameters associated with the vascular function and the hemodynamics of the subject are determined based on the extracted pixel values representing biosignals. The determined parameters can serve as potential biomarkers of vascular dysfunction and hemodynamic imbalances. The vascular health condition of the subject is evaluated based on deviation of the determined one or more parameters with respect to predetermined parameters, on comparison of the determined parameters with the predetermined parameters. Thus, it would be appreciated that the vascular health condition is evaluated by a non-invasive method without any physical contact to the subject and does not involve any harmful radiation.

In an embodiment, the determined one or more parameters associated with the vascular function correspond to time and frequency domain parameters which can be any or a combination of average intensity, signal amplitude, signal period, signal entropy, signal power spectral density, histogram and peak count. The time and frequency domain parameters can be associated with any or a combination of hemodynamics, general healthiness of the artery itself or the physiological data which may indicate the core temperature, blood flow velocity, blood density, arterial stiffness, oxygen saturation in blood, and the like. These potential biomarkers indicate the vascular health and hemodynamic changes in a person.

In an exemplary embodiment, the disclosed system and method can be used for various applications, for example to determine the scale or severity of vascular dysfunction in a person, determine the influence of the peripheral vascular, cardiovascular and cerebrovascular disorders on the vascular health, early detection of biomarkers indicating the development of the vascular dysfunction, and to determine the efficacy of lifestyle and medical interventions.

Various objects, features, aspects and advantages of the inventive subject matter will become apparent from the following detailed description of preferred embodiments, along with the accompanying drawing figures in which like numerals represent like components.

BRIEF DESCRIPTION OF THE DRAWINGS

In the figures, similar components and/or features may have the same reference label. Further, various components of the same type may be distinguished by following the reference label with a second label that distinguishes among the similar components. If only the first reference label is used in the specification, the description is applicable to any one of the similar components having the same first reference label irrespective of the second reference label.

DETAILED DESCRIPTION

Figure 1:
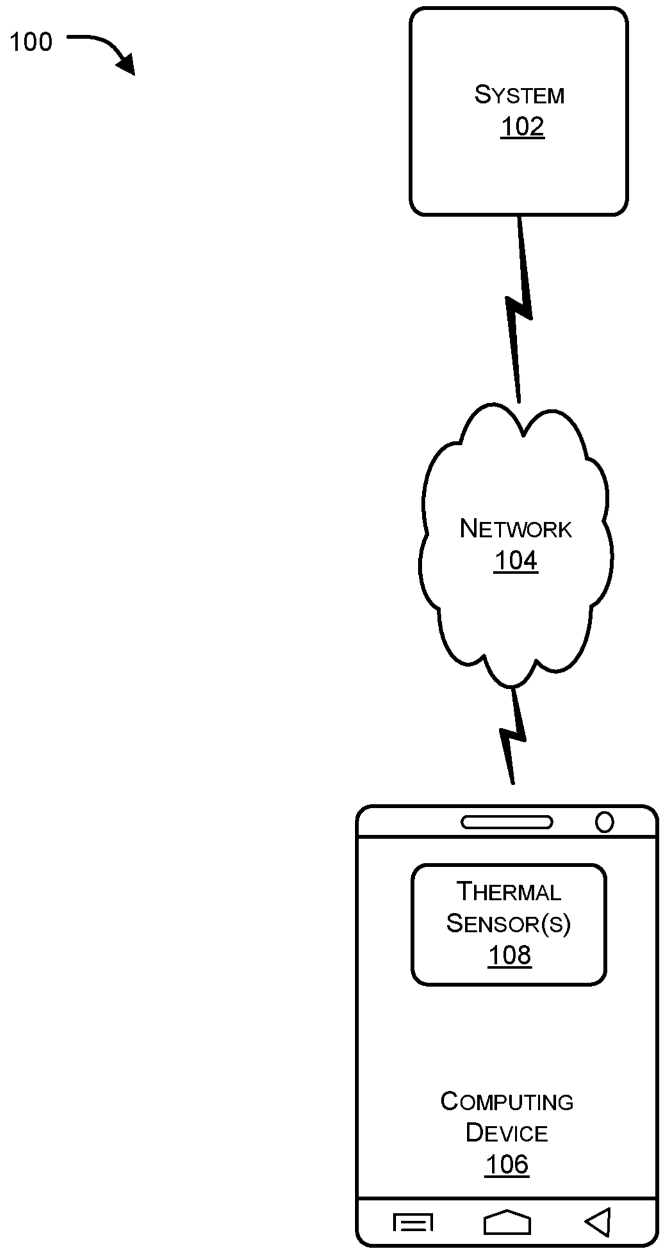
FIG. 1 illustrates an exemplary overall architecture in which or with which the proposed system can be implemented, in accordance with an embodiment of the present disclosure.

The following is a detailed description of embodiments of the disclosure depicted in the accompanying drawings. The embodiments are in such detail as to communicate the disclosure. However, the amount of detail offered is not intended to limit the anticipated variations of embodiments; on the contrary, the intention is to cover all modifications, equivalents, and alternatives falling within the spirit and scope of the present disclosure as defined by the appended claims.

If the specification states a component or feature "may", "can", "could", or "might" be included or have a characteristic, that particular component or feature is not required to be included or have the characteristic. As used in the description herein and throughout the claims that follow, the meaning of "a," "an," and "the" include plural reference unless the context clearly dictates otherwise. Also, as used in the description herein, the meaning of "in" includes "in" and "on" unless the context clearly dictates otherwise.

Various methods described herein may be practiced by combining one or more machine-readable storage media containing the code according to the present invention with appropriate standard computer hardware to execute the code contained therein. An apparatus for practicing various embodiments of the present invention may involve one or more computers (or one or more processors within the single computer) and storage systems containing or having network access to a computer program(s) coded in accordance with various methods described herein, and the method steps of the invention could be accomplished by modules, routines, subroutines, or subparts of a computer program product.

While embodiments of the present invention have been illustrated and described, it is apparent that the invention is, not limited to these embodiments only. Numerous modifications, changes, variations, substitutions, and equivalents will be apparent to those skilled in the art, without departing from the spirit and scope of the invention, as described in the claim.

Embodiments explained herein relate to health care systems for evaluating the health condition of an individual/patient. In particular, the present disclosure relates to a non-contact, non-invasive passive system and method for determining the vascular health condition of a person.

The vascular dysfunctions if not intervened in the early stages stimulate structural atherosclerosis. Studies have shown that interventions are effective in reversing vascular dysfunction and reducing or delaying the risk of structural atherosclerosis. Hence, a simple, non-invasive, non-contact technique that facilitates the monitoring of vascular health conditions more frequently and in the early stages, improving people's quality of life, reducing the risks and avoiding the complications of developing fatal diseases. Thus, the present disclosure provides an arrangement for individuals to take precautionary steps to delay the onset of the metabolic disorders or to lower the rate of progression of existing disorders in chronic patients. The disclosed system and method are based on the principle of using the temperature distribution observed in the body to measure parameters indicating structural and functional characteristics of the vascular metabolism. The functioning of the vital organs is associated with the metabolic heat, which is transferred to the skin surface by the circulating blood. Any dysfunction, namely atherosclerosis that occurs in blood vessels causes the heat distribution observed to differ from the heat distribution of the skin observed under healthy conditions.

In an aspect, the present disclosure provides a system and method for measuring the vascular health condition of a person. The system and method includes capturing a passive infrared thermal image(s) and/or video(s) of at least one part of the body of the subject. Thermal cameras used for capturing these thermal videos senses the infrared radiation emitted from the body and produces images representing the spatial intensity of radiation. This system and method provides the benefit of not needing any physical connection to the person and does not have any external energy radiations penetrating the body of the person. The system and method includes processing the captured thermal image/video(s) using image processing techniques to detect a region of interest from the predefined body part in the frame of the captured images and/or video. The region of interest includes the vascular structure that needs to be examined. The detected region is further tracked in the successive frames and segmented based on a gradient of thermal pattern. The region of interest is segmented using edge detection, morphological operations and contour approximation.

In an embodiment, the system and method uses the segmented region to extract pixel values from each of the frames of captured images and/or videos for determining the changes in the temperature over time. The pixel values in the region of interest can be spatially transformed to obtain a quantitative representation for the pattern observed in each frame of captured images and/or video, representing a set of biosignals associated with pulsatile nature of the blood flow. The extracted values are normalized and filtered to remove the noise. The filtered data is evaluated by applying statistical analysis and signal processing techniques to determine time and frequency domain parameters which may serve as the potential biomarkers for the vascular health condition of the person.

These parameters can then be compared to their predetermined reference parameters to identify possible vascular dysfunction, the relative influence of a known disorder on the vascular health of the person. The deviation of the parameters from its normal range to a higher or a lower value indicates an abnormality and/or difference in the parameter value measured at different locations indicate a blockage in the region. These imbalances can be further analyzed to determine the possible dysfunction of the vascular structure. In an exemplary embodiment, the set of reference parameters are initially determined by processing the thermal video and/or images of a set of individuals with known vascular health conditions and analyzing the distribution of values evaluated for each of the parameters. The method automatically identifies the vascular impairments without a need for intervention from a medical professional.

FIG. 1 illustrates an exemplary overall architecture in which or with which the proposed system can be implemented in accordance with an embodiment of the present disclosure.

In an aspect, an overall architecture 100 comprises a system 102 that can be implemented in any computing device that can be configured/operatively coupled with a server. The server can be located at local, and/or remote and/or cloud locations or the server can be a database to store set of instructions, for example a first set of instructions, a second set of instructions, and/or other required data/instructions to be used by the system 102. The system 102 can include one or more processors coupled to a memory storing a set of instructions executable by the processors. The system 102 can be implemented using any or a combination of hardware components and/or software components such as a server, a computing system, a computing device, a security device and the like, such that system can determine the vascular health condition of a subject such as an human. Further, the system 102 can be communicatively coupled with a computing device 106 through a network 104. The computing device 106 can be integrated with a set of thermal sensors 108. The set of thermal sensors (hereinafter, also referred to as imaging device) 108 can be any or a combination, but not limited to, a digital camera, a digital single-lens reflex (DSLR) camera, or a standalone infrared camera, a monochromatic camera and a thermal camera. Those skilled in the art would appreciate that a thermal image can be captured using the thermal camera, the thermal camera senses thermal or infrared radiation emitted from the body of the person and can render images representing the spatial intensity of radiation. Since the images can be captured from an optimal distance, therefore this technique is non-invasive and non-contact.

The network 104 can be a wireless network, a wired network or a combination thereof that can be implemented as one of the different types of networks, such as Intranet, Local Area Network (LAN), Wide Area Network (WAN), Internet, and the like. Further, the network 104 can either be a dedicated network or a shared network. The shared network can represent an association of the different types of networks that can use a variety of protocols, for example, Hypertext Transfer Protocol (HTTP), Transmission Control Protocol/Internet Protocol (TCP/IP), Wireless Application Protocol (WAP), and the like.

Examples of the computing devices 106 can include but are not limited to, a portable computer, a personal digital assistant, a handheld device, and a workstation. In an embodiment, the computing device 106 is a mobile phone having the imaging device 108. In another embodiment, the imaging device 108 is operatively coupled with the computing device 106. In an embodiment, system 102 facilitates a non-invasive and non-contact technique for determining biomarkers to help determine the vascular health condition of the person.

In an embodiment, the camera 108 can be used for capturing thermal images or thermal video of at least one body parts, such as a face, of the subject. For example, the length of the captured thermal video may range from thirty seconds to one minute. According to an embodiment, during pre-processing the system 102 can receive a set of data packets associated with the captured one or more thermal images or the captured thermal video from the camera and process a set of frames in the captured thermal video or the captured one or more thermal images.

In an embodiment, the system 102 can be configured to detect a predefined region of the at least one body part of the subject in each frame of the captured any or a combination of the one or more images and videos, and segment one or more portions, such as a forehead or a portion of the forehead of the subject, from the detected predefined region in each frame of the captured any or a combination of the one or more images and videos to identify a region of interest comprising one or more blood vessels in the one or more segmented portions. The system 102 extracts one or more pixel values, representing a set of biosignals, from each frame of the captured any or a combination of the one or more images and videos based on the identified region of interest to determine one or more parameters associated with the vascular functions and hemodynamics of the subject based on the extracted one or more pixel values representing the set of biosignals. The determined parameters can be associated with potential biomarkers of vascular dysfunctions and hemodynamic imbalances. Further, the system 102 compare the determined one or more parameters associated with the vascular function and hemodynamics with predetermined reference parameters to evaluate the vascular health condition of the subject based on deviation of the determined one or more parameters with respect to the predetermined reference parameters data on the basis of comparison. The predetermined reference parameters can stored in the database.

The determined one or more parameters associated with the vascular function and hemodynamics can correspond to time and frequency domain parameters which can be any or a combination of average intensity, signal amplitude, signal period, signal entropy, signal power spectral density, histogram and peak count. The time and frequency domain parameters can also be associated with any or a combination of general healthiness of the artery itself or the physiological data which may indicate the core temperature, blood flow velocity, blood density, arterial stiffness, and oxygen saturation in blood.

In an embodiment, evaluation of the vascular health condition of the subject considers the demographics and medical history of the subject along with the determined parameters for evaluating the vascular health condition.

In an embodiment, the processors of the system 102 can be configured to segment the identified region of interest from each of the captured any or a combination of the one or more images and videos based on the difference between thermal intensity along the one or more blood vessels and a thermal intensity in other regions of the one or more segmented portions. The identified region of interest can be segmented using any or a combination of morphological operations, otsu thresholding, edge detection and contour approximations techniques.

In an embodiment, the processors can execute the first set of instructions associated with image filtering and enhancing techniques on each of the captured any or a combination of the one or more images and videos for removing noise and improving quality.

In an embodiment, the processors can execute a second set of instruction associated with image processing including feature detection and landmark detection to detect the predefined region of the at least one body part in each frame of the captured any or a combination of the one or more images and videos on receipt of the set of data packets.

In an embodiment, the processors of the system 102 can be configured to perform spatial transformation on the identified region of interest to obtain a quantitative representation of a pattern observed in each frame of the captured any or a combination of the one or more images and videos, representing the set of biosignals waveform along an arterial section associated with pulsatile nature of blood flow.

In an embodiment, the processors of the system 102 can be configured to determine time domain values by applying statistical analysis on the extracted one or more pixel values representing the set of biosignals to determine frequency domain values by applying normalization, Fast Fourier Transform and frequency filtering technique on the determined time domain values.

In an embodiment, the processors can determine, using signal processing techniques on the set of biosignals, the time and frequency domain parameters based on the determined frequency domain values and time domain values.

Figure 2:
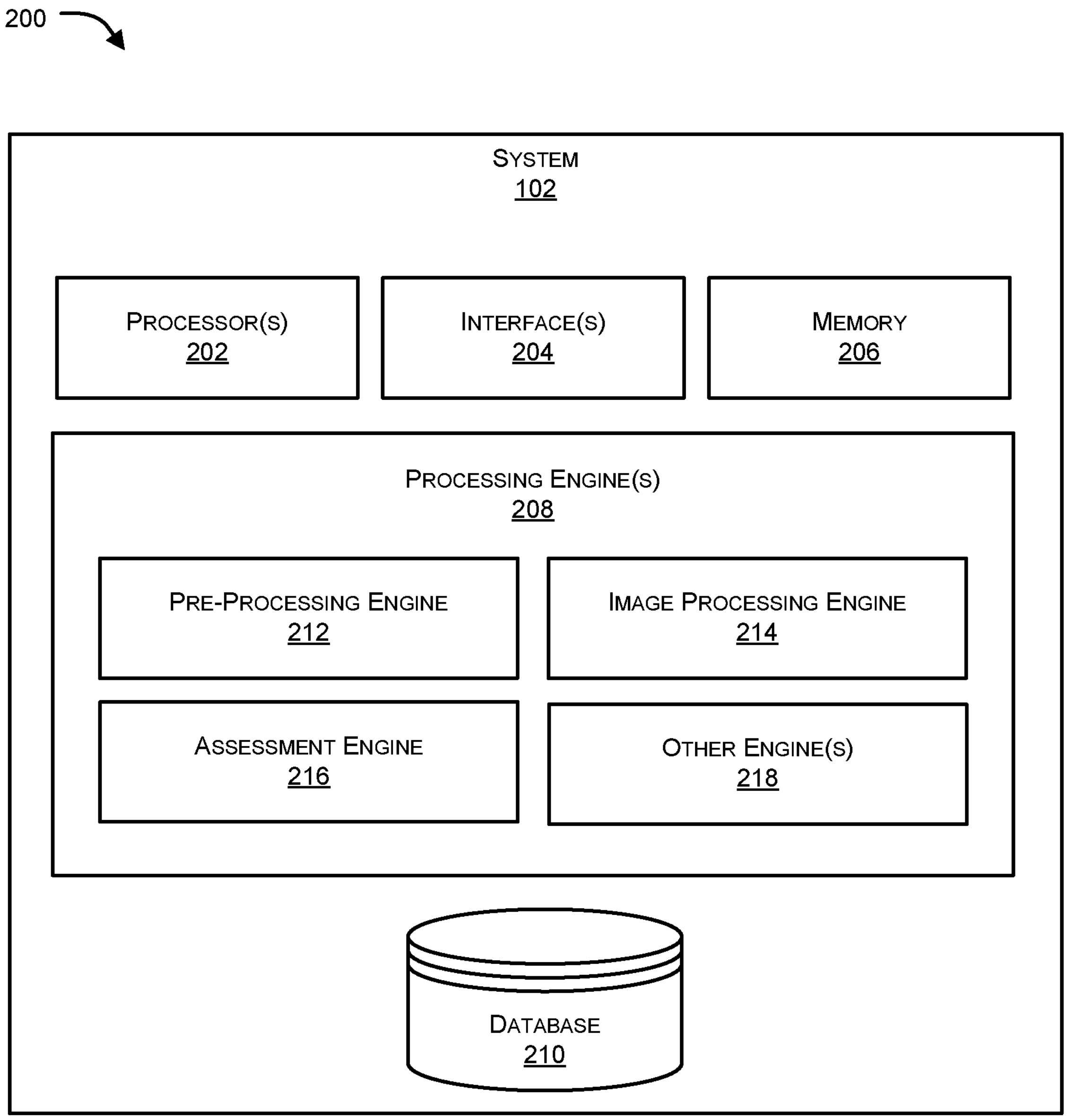
FIG. 2 illustrates exemplary functional components of a system, in accordance with an embodiment of the present disclosure.

FIG. 2 illustrates the exemplary functional components of a system by considering an example, in accordance with an embodiment of the present disclosure.

In an aspect, the system 102 may comprise one or more processor(s) 202. The one or more processor(s) 202 may be implemented as one or more microprocessors, microcomputers, microcontrollers, digital signal processors, central processing units, logic circuitries, and/or any device that manipulates data based on operational instructions. Among other capabilities, the one or more processor(s) 202 are configured to fetch and execute computer-readable instructions stored in a memory 206 of the system 102. The memory 206 may store one or more computer-readable instructions or routines, which may be fetched and executed to create or share the data units over a network service. The memory 206 may comprise any non-transitory storage device including, for example, volatile memory such as RAM, or non-volatile memory such as EPROM, flash memory, and the like.

The system 102 may also comprise an interface(s) 204. The interface(s) 204 may comprise a variety of interfaces, for example, interfaces for data input and output devices, referred to as IO devices, storage devices, and the like. The interface(s) 204 may facilitate communication of system 102 with various devices coupled to the system 102 such as the input unit 102 and the output unit 106. The interface(s) 204 may also provide a communication pathway for one or more components of the system 102. Examples of such components include, but are not limited to, processing engine(s) 208 and data (hereinafter, also referred to as database) 210.

The processing engine(s) 208 may be implemented as a combination of hardware and programming (for example, programmable instructions) to implement one or more functionalities of the processing engine(s) 208. In examples described herein, such combinations of hardware and programming may be implemented in several different ways. For example, the programming for the processing engine(s) 208 may be processor-executable instructions stored on a non-transitory machine-readable storage medium and the hardware for the processing engine(s) 208 may comprise a processing resource (for example, one or more processors), to execute such instructions. In the present examples, the machine-readable storage medium may store instructions that, when executed by the processing resource, implement the processing engine(s) 208. In such examples, the system 102 may comprise the machine-readable storage medium storing the instructions and the processing resource to execute the instructions, or the machine-readable storage medium may be separate but accessible to system 102 and the processing resource. In other examples, the processing engine(s) 208 may be implemented by electronic circuitry.

The database 210 may comprise data that can be either stored or generated as a result of functionalities implemented by any of the components of the processing engine (s) 208. The database 210 may store set of instructions, for example a first set of instructions, a second set of instructions, and/or other required predetermined parameters data/instructions/algorithms to be used by the processors/processing engine 208.

In an exemplary embodiment, the processing engine(s) 208 may comprise a pre-processing engine 212, an image processing engine 214, an assessment engine 216 and other engines(s) 218.

It would be appreciated that modules being described are only exemplary modules, and any other module or sub-module may be included as part of the system 102. These modules too may be merged or divided into super-modules or sub-modules as may be configured.

Pre-Processing Engine 212

Figure 4A:
FIG. 4A illustrates a sequence of frames from the thermal video captured using the infrared thermal camera, in accordance with an embodiment of the present disclosure.
Figure 4B:
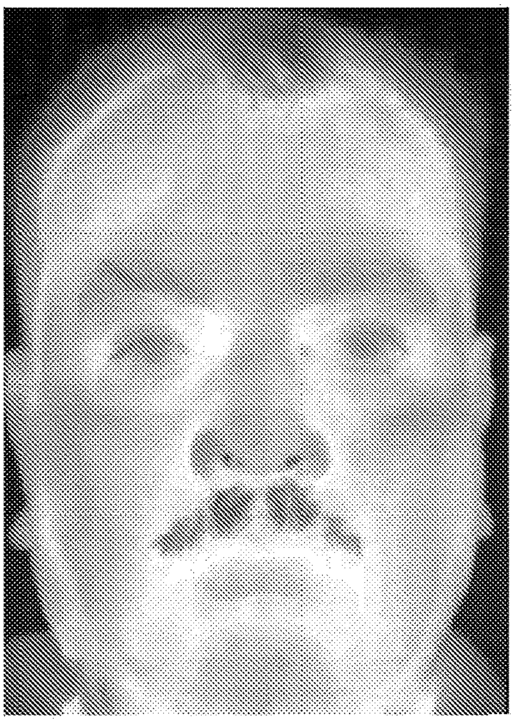
FIG. 4B illustrates a segment of the facial region detected using the face detection algorithm and extracted from the thermal images captured, in accordance with an embodiment of the present disclosure.

In an aspect, the pre-processing engine 212 receives a sequence of thermal image and/or video frames, comprising the image of the required body part, from the thermal sensor 108 of the computing device 106. FIG. 4A depicts an instance of the implementation involving the sequence of thermal image frames consisting of anterior face obtained from the camera. The received thermal image frames may be converted into grayscale for processing. Further, the pre-processing engine 212 applies image filtering and enhancement techniques on the received frames to remove noise and ensure the quality of the thermal images is sufficient before processing. The pre-processing engine 212 then may use various detection algorithms/instructions, for example a haar cascade classifier for face detection on each of the frames in order to detect a predefined body part like a face in the frames as shown in FIG. 4B. The pre-processing engine 212 may reject a captured thermal video or image from the captured videos and/or images when the defined part is not detected. Further, the pre-processing engine 212 also may use tracking methods to detect and extract the defined region (hereinafter, also referred to as predefined region) in subsequent frames to ensure a uniform set of frame segments.

In an embodiment, in order to ensure faster processing, the pre-processing engine 212 may perform contrast stretching, which is efficient as well as a computationally cheap technique implemented to enhance image quality. Those skilled in the art would appreciate that the pre-processing engine 212 focuses on enhancement and performs certain operations on the input image frames to ensure that processing in subsequent stages through the implementation of various other engines can be performed in less computational time. The enhancement of image frames can further be optimized to stay free from floating-point operations.

Image Processing Engine 214

Figure 4C:
FIG. 4C illustrates a forehead region segmented from the face to identify the region of interest comprising the blood vessels, in accordance with an embodiment of the present disclosure.

In an embodiment, the image processing engine 214 receives the pre-processed frames of the thermal video/images including the predefined region segmented from the background of the frames. The image processing engine 214 may use landmark detection or feature detection algorithms on the set of preprocessed frames to determine a position of certain markers or identifiers on the predefined region, such as the eyes and the nose on the facial region of the frames as shown in FIG. 4B. The positions of the landmarks obtained are further used to segment the area comprising the blood vessels, such as the forehead region from the set of the preprocessed frames as shown in FIG. 4C. In another embodiment, the image processing engine 214 further may define a region of interest for each image frame from a set of image frames received from the pre-processing engine 212. The region of interest may comprise one or more blood vessels within the segmented area such as the branches of the arteries in the forehead region. For example, the defined region of interest (ROI) may be segmented based on the heat distribution on the forehead. The image processing engine 214 may use a bilateral 2D filter on the segmented area in each of the preprocessed frames to remove noise while preserving the edge due to the thermal intensity gradient. Further, since the region of interest comprising the blood vessel is brighter than the remaining sections of the segmented area due to the heat emitted during blood flow, the ROI in each of the frames is segmented using a combination of morphological operations such as erosion and opening operation followed by Otsu thresholding, edge detection and contour approximations. The ROI extracted from each of the set of frames resembles the vascular structure.

In an exemplary embodiment, image segmentation is the process of partitioning a digital image into multiple regions or sets of pixels. Mostly, image partitions are different objects which have the same texture or color. The image segmentation results are a set of regions that cover the entire image together and a set of contours extracted from the image. All of the pixels in a region are similar with respect to some characteristics such as color, intensity, or texture. Adjacent regions are considerably different with respect to the same individuality. The different approaches include but are not limited to (i) by finding boundaries between regions based on discontinuities in intensity levels, (ii) thresholds based on the distribution of pixel properties, such as intensity values, and (iii) based on finding the regions directly. Thus, the choice of an image segmentation technique is depending on the problem being considered.

Region-based methods are based on continuity. These techniques divide the entire image into sub-regions depending on some rules like all the pixels in one region must have the same grey level. Region-based techniques rely on common patterns in intensity values within a cluster of neighboring pixels. The cluster is referred to as the region in addition to group the regions according to their anatomical or functional roles are the goal of the image segmentation. A threshold is the simplest way of segmentation. Using thresholding technique regions can be classified on the basis of range values, which is applied to the intensity values of the image pixels. Thresholding is the transformation of an input image to an output that is a segmented binary image—segmentation methods based on finding the regions for abrupt changes in the intensity value.

When images are processed for enhancement, and while performing some operations like thresholding, more is the chance for distortion of the image due to noise. As a result, imperfections exist in the structure of the image. The primary goal of the morphological operation is to remove this imperfection that mainly affects the shape and texture of images. It is evident that morphological operations can be instrumental in image segmentation as the process directly deals with 'shape extraction' in an image. Morphology in the context of image processing means the description of the shape and structure of the object in an image. Morphological operations work on the basis of set theory and rely more on the relative ordering of the pixel instead of the numerical value. This characteristic makes them more useful for image processing. Those skilled in the art would appreciate the significance of these techniques in image segmentation.

Figure 4D:
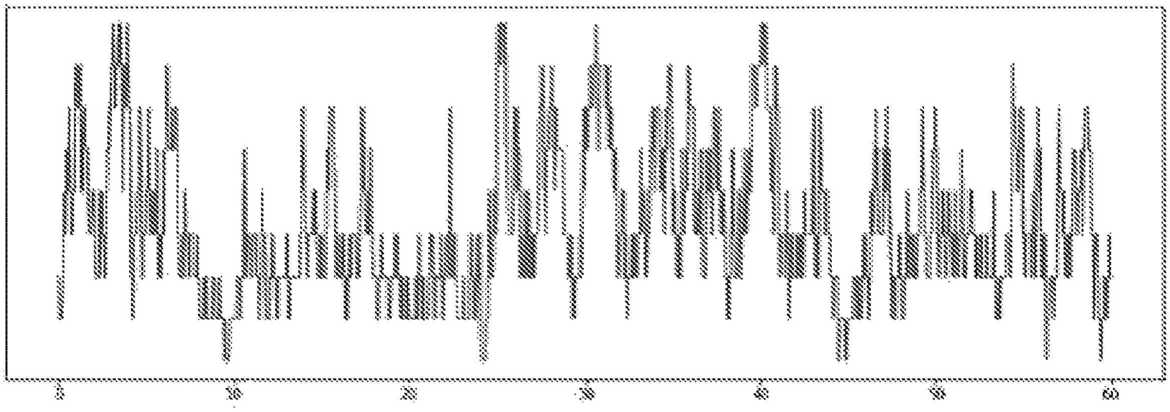
FIG. 4D illustrates an exemplary biosignal waveform determined from the pixel values extracted from the region of interest, in accordance with an embodiment of the present disclosure.

In an embodiment, the image processing engine 214 uses the obtained ROI to extract pixel values from each of the frames for describing the changes in the temperature over time. The change in these pixel values correlates with the transmission of the blood through the arterial cross-section. The pixel values in the region of interest are spatially transformed to obtain a quantitative representation for the pattern observed in each frame. The spatial transformation includes applying block-based averaging functions and determining the maximum pixel intensity value along the cross-sectional axis. The values can be represented as a series—

$$X(t)_1^T = \mathrm{Max}_{i=0,j=0}^{i+B_w<=w,j+B_h<=h}\left[\left(\sum_{x=i}^{B^w}\sum_{y=j}^{B_h}P(x,y)\right)/(B_w)*B_h\right]$$

where X(t) is the time domain value for the frame t, P(x,y) is the pixel intensity at position (x,y), $B_w$, $B_h$ is the width and height of the block. The extracted values are represented as a set of one or more time domain biosignals which are then used by other modules/engines to evaluate and measure parameters related to vascular health and hemodynamics. FIG. 4D illustrates an exemplary biosignal waveform extracted from the region of interest of an individual.

Assessment Engine 216

In an embodiment, the assessment engine 216 is used for determining the vascular health condition by determining parameters pertaining to the structural and functional impairment of the blood vessels and comparing with the parameters previously determined in another embodiment using the set of individuals with known vascular health conditions. The set of one or more biosignals extracted from the image processing engine 214 can be initially normalized using min-max normalization. The normalized time data is then transformed to obtain frequency domain data using the function, P(X)

$$\omega(k)_0^T = F_{f=0.67}^{1.67}\left[\sum_{n=0}^{N}X[n]e^{(-2\pi ikn)/N}\right]$$

where the assessment engine 216 uses Fast Fourier Transform on the data to obtain frequency domain values. The frequency values are then filtered 'F' to select the frequencies in between 0.67 Hz and 1.7 Hz in order to select the signal in the frequency range of the pulse. The assessment engine 216 further applies signal processing techniques on these filtered data to determine time and frequency domain parameters such as, but not limited to, average intensity, signal amplitude, signal period, signal entropy, signal power spectral density, histogram and peak count for each of the set of biosignals extracted independently. The combination of one or more of these parameters is associated with hemodynamics and vascular function. This assessment is subject to thermal pattern analysis and signals analysis on the pulsatile nature of thermal changes in accordance with the pulsatile blood flow.

In another embodiment, before developing the assessment engine 216, individuals diagnosed with one or more vascular disorders such as diabetes, hypertension, dyslipidemia and/or coronary artery disease are tested using conventional methods like carotid doppler ultrasound. Carotid doppler ultrasound measures the extent of vascular dysfunction based on the blood flow and the plaque formation observed in the arteries. The calculated signal parameters of these individuals, the results obtained from the ultrasound test, and the signal parameters of other healthy individuals are analyzed and compared using statistical models to identify the relations between the signal parameters from thermal images and carotid ultrasound doppler test results. Mathematical model is built to evaluate the vascular health condition equivalent to the results obtained from the ultrasound. The vascular health condition determined using the mathematical model can be represented over a scale of zero to one or one to ten referring to the severity of the condition.

Figure 3:
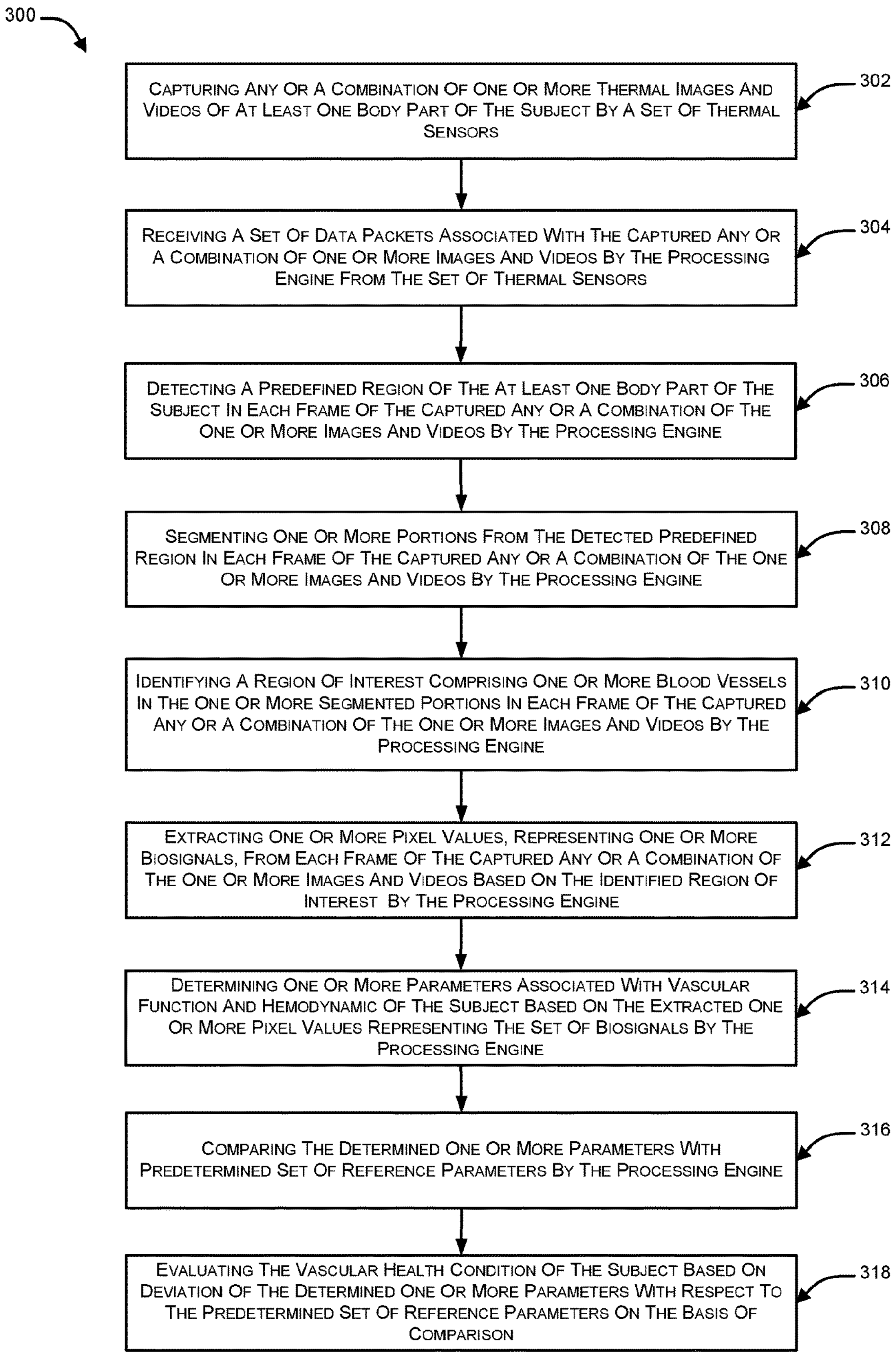
FIG. 3 illustrates a flow diagram illustrating a process for determining the health condition of a person, in accordance with an embodiment of the present disclosure.

FIG. 3 illustrates a flow diagram illustrating a process for measuring the vascular health condition of a person in accordance with an embodiment of the present disclosure.

In an aspect, the proposed method may be described in the general context of computer-executable instructions. Generally, computer-executable instructions include routines, programs, objects, components, data structures, procedures, modules, functions, etc. that perform particular functions or implement particular abstract data types. The method can also be practiced in a distributed computing environment where functions are performed by remote processing devices that are linked through a communications network. In a distributed computing environment, computer-executable instructions may be located in both local and remote computer storage media, including memory storage devices.

The order in which the method as described is not intended to be construed as a limitation and any number of the described method blocks may be combined in any order to implement the method or alternate methods. Additionally, individual blocks may be deleted from the method without departing from the spirit and scope of the subject matter described herein. Furthermore, the method may be implemented in any suitable hardware, software, firmware, or combination thereof. However, for ease of explanation, in the embodiments described below, the method may be considered to be implemented in the above-described system.

In an aspect, the proposed method may be implemented with assistance of the above discussed system.

In the context of the flow diagram 300, a block 302 pertains to capturing any or a combination of one or more thermal images and videos of at least one body part, for example a face, of the subject by a set of thermal sensors which are operatively coupled to a processing engine having one or more processors.

Further, a block 304 pertains to receiving a set of data packets associated with the captured any or a combination of one or more images and videos by the processing engine from the set of thermal sensors. The processing engine may perform pre-processing on the thermal images or thermal videos received from the set of thermal sensors for noise reduction and quality enhancement.

Further, a block 306 pertains to detecting a predefined region of the at least one body part of the subject in each frame of the captured any or a combination of the one or more images and videos by the processing engine based on the receipt of the set of data packets.

Further, a block 308 pertains to segmenting one or more portions from the detected predefined region in each frame of the captured any or a combination of the one or more images and videos by the processing engine.

Further, a block. 310 pertains to identifying a region of interest comprising one or more blood vessels in the one or more segmented portions in each frame of the captured any or a combination of the one or more images and videos by the processing engine.

Further, a block 312 pertains to extracting one or more pixel values, representing one or more biosignals, from each frame of the captured any or a combination of the one or more images and videos based on the identified region of interest by the processing engine.

Further, a block 314 pertains to determining one or more parameters associated with vascular function and hemodynamic of the subject based on the extracted one or more pixel values representing the set of biosignals by the processing engine.

Further, a block 316 pertains to comparing the determined one or more parameters with predetermined set of reference parameters by the processing engine. In an exemplary embodiment, the predetermined reference parameters can be determined by processing the thermal images/videos of a set of individuals with known vascular health conditions and analyzing the distribution of values evaluated for each of the parameters, and stored for further use.

Further, a block 318, pertains to evaluating the vascular health condition of the subject based on deviation of the determined one or more parameters with respect to the predetermined set of reference parameters on the basis of comparison. In an embodiment, determined parameters can then be processed using computational models to determine the vascular health condition or to determine the influence of the underlying disorders on the vascular dysfunction based on the deviations and the imbalances in the parameters.

Thus, the present disclosure provides a system and method for evaluating the vascular health condition of a person using non-invasive and non-contact passive thermal imaging techniques for measuring biomarkers indicating chronic vascular dysfunction. Vascular dysfunction is often seen with people who suffer from chronic metabolic disorders and plays a vital role in the progression of peripheral neuropathy, cardiovascular and cerebrovascular diseases. The thermal pattern of a vascular structure, which is observed through the thermal imaging of the person is used to determine the biomarkers pertaining to the vascular dysfunction of the person. The system and method includes capturing passive thermal image(s) and/or video(s) from one or more regions of the body of the person, segmenting the required region of interest from these thermal image(s) and/or video(s), and extracting features based on the thermal pattern. Thermal patterns observed from these thermo-grams are analyzed and converted into biosignals for processing. Various signal processing methods are performed on these biosignals and desired features are extracted. These features such as, but not limited to, include average intensity, interquartile range, wavelength, signal entropy, frequency power, histogram, act as the potential biomarkers of the vascular dysfunction indicating structural and functional changes. These biomarkers may be used for identifying the progression of atherosclerosis, arteriosclerosis or changes in hemodynamics. As a clinical application, these measured biomarkers may be used in the preliminary diagnosis and monitoring of non-communal diseases like diabetes, hypertension and other cardio and cerebrovascular risk factors.

Thus, it will be appreciated by those of ordinary skill in the art that the diagrams, schematics, illustrations, and the like represent conceptual views or processes illustrating systems and methods embodying this invention. The functions of the various elements shown in the figures may be provided through the use of dedicated hardware as well as hardware capable of executing associated software. Similarly, any switches shown in the figures are conceptual only. Their function may be carried out through the operation of program logic, through dedicated logic, through the interaction of program control and dedicated logic, or even manually, the particular technique being selectable by the entity implementing this invention. Those of ordinary skill in the art further understand that the exemplary hardware, software, processes, methods, and/or operating systems described herein are for illustrative purposes and, thus, are not intended to be limited to any particular name.

While embodiments of the present invention have been illustrated and described, it is apparent that the invention is not limited to these embodiments only. Numerous modifications, changes, variations, substitutions, and equivalents will be apparent to those skilled in the art, without departing from the spirit and scope of the invention, as described in the claim.

In the foregoing description, numerous details are set forth. It is apparent, however, to one of ordinary skill in the art having the benefit of this disclosure, that the present invention may be practiced without these specific details. In some instances, well-known structures and devices are shown in block diagram form, rather than in detail, to avoid obscuring the present invention.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously. Within the context of this document terms "coupled to" and "coupled with" are also used euphemistically to mean “communicatively coupled with” over a network, where two or more devices are able to exchange data with each other over the network, possibly via one or more intermediary devices.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms “comprises” and “comprising” should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

While the foregoing describes various embodiments of the invention, other and further embodiments of the invention may be devised without departing from the basic scope thereof. The scope of the invention is determined by the claims that follow. The invention is not limited to the described embodiments, versions or examples, which are included to enable a person having ordinary skill in the art to make and use the invention when combined with information and knowledge available to the person having ordinary skill in the art.

Advantages of the Present Disclosure

The present disclosure provides an improved system for evaluating the vascular health condition of an individual.

The present disclosure provides an efficient system for early detection of biomarkers in individuals indicating vascular dysfunction.

The present disclosure provides a non-contact, non-invasive system and method to determine hemodynamic imbalances and vascular complications of a person using thermal imaging to help in diagnosis of the health conditions.

The present disclosure provides an efficient system and method using biomarkers associated with vascular structure and functions measured from thermal imaging for assessing vascular health of an individual;

The present disclosure provides a simple and cost-effective system and method which can be easily implemented for evaluating the vascular health condition as well as hemodynamic imbalances of a person to help in diagnosis of the health conditions.

We claim:

1. A system for evaluating a vascular health condition of a subject, the system comprising:

a set of thermal sensors for capturing one or more thermal images and/or videos of at least one body part of the subject; and a processing engine operatively coupled to the set of thermal sensors, and comprising one or more processors coupled to a memory, the memory storing a set of instructions executable by the one or more processors to:

receive a set of data packets associated with the captured one or more thermal images and/or videos from the set of thermal sensors;

in response to the receipt of the set of data packets, detect, using one or more detection algorithms, a predefined region of the at least one body part of the subject in each frame of the captured one or more thermal images and/or videos;

segment one or more portions from the detected predefined region in each frame of the captured one or more thermal images and/or videos based on a difference between a thermal intensity along one or more blood vessels and a thermal intensity in other regions of the one or more segmented portions;

identify a region of interest comprising the one or more blood vessels in the one or more segmented portions in each frame of the captured one or more thermal images and/or videos;

extract one or more pixel values, representing a set of biosignals, from each frame of the captured one or more thermal images and/or videos based on the identified region of interest;

determine one or more parameters associated with vascular functions and hemodynamics of the subject based on the extracted one or more pixel values representing the set of biosignals;

compare the determined one or more parameters associated with the vascular functions and hemodynamics with a predetermined set of reference parameters;

evaluate the vascular health condition of the subject based on deviation of the determined one or more parameters with respect to the predetermined set of reference parameters on the basis of the comparison, wherein the evaluation of the vascular health condition of the subject considers demographics and medical history of the subject along with the determined one or more parameters;

wherein one or more frames from the captured one or more thermal images and/or videos are rejected when the predefined region is not detected in the one or more frames; and wherein the identified region of interest is segmented using a combination of morphological operations comprising erosion and opening operation, followed by Otsu thresholding, edge detection and contour approximation techniques.

2. The system as claimed in claim 1, wherein the set of thermal sensors are associated with one or more of a digital camera, a digital single-lens reflex (DSLR) camera, and an infrared thermal camera, and wherein the set of thermal sensors sense heat or infrared radiation emitted from the at least one body part of the subject and renders the one or more thermal images and/or videos representing a spatial intensity of radiation.

3. The system as claimed in claim 1, wherein the determined one or more parameters are associated with potential biomarkers of vascular dysfunctions and hemodynamic imbalances, and wherein the predetermined set of reference parameters are stored in a database operatively coupled to the processing engine.

4. The system as claimed in claim 1, wherein the subject is a human.

5. The system as claimed in claim 1, wherein the at least one body part of the subject is a face of the subject, and the segmented one or more portions are associated with a forehead or a portion of the forehead of the subject.

6. The system as claimed in claim 1, wherein the one or more processors are configured to execute a first set of instructions associated with image filtering and enhancing techniques on each of the captured one or more thermal images and/or videos for removing noise and improving quality.

7. The system as claimed in claim 1, wherein the one or more processors are configured to execute a second set of instructions associated with image processing including feature detection and landmark detection to detect the predefined region of the at least one body part in each frame of the captured one or more thermal images and/or videos on receipt of the set of data packets.

8. The system as claimed in claim 1, wherein the one or more processors are configured to perform spatial transformation on the identified region of interest to obtain a quantitative representation of a pattern observed in each frame of the captured one or more thermal images and/or videos, the quantitative representation representing the set of biosignals as a waveform along an arterial section associated with a pulsatile nature of blood flow.

9. The system as claimed in claim 1, wherein the one or more processors are configured to determine time domain values by applying statistical analysis on the extracted one or more pixel values representing the set of biosignals.

10. The system as claimed in claim 9, wherein the one or more processors are configured to determine frequency domain values by applying normalization, Fast Fourier Transform and frequency filtering technique on the determined time domain values.

11. The system as claimed in claim 10, wherein the one or more processors are configured to determine, using signal processing techniques on the set of biosignals, time and frequency domain parameters based on the determined frequency domain values and time domain values, and wherein the determined one or more parameters associated with the vascular function and hemodynamics correspond to the time and frequency domain parameters.

12. The system as claimed in claim 11, wherein the time and frequency domain parameters are one or more of average intensity, signal amplitude, signal period, signal entropy, signal power spectral density, histogram and peak count, and wherein the time and frequency domain parameters are also associated with one or more of the hemodynamics, general healthiness of the one or more blood vessels, and physiological data which may indicate core temperature, blood flow velocity, blood density, arterial stiffness, and oxygen saturation in blood.

13. A method for measuring a vascular health condition of a subject, the method comprising:

capturing, by a set of thermal sensors, one or more thermal images and/or videos of at least one body part of the subject;

receiving, by a processing engine, a set of data packets associated with the captured one or more thermal images and/or videos from the set of thermal sensors operatively coupled to the processing engine;

performing contrast stretching on the captured one or more thermal images and/or videos;

optimizing the contrast stretching to exclude floating-point operations;

detecting, by the processing engine, using one or more detection algorithms, a predefined region of the at least one body part of the subject in each frame of the captured one or more thermal images and/or videos in response to receipt of the set of data packets;

segmenting, by the processing engine, one or more portions from the detected predefined region in each frame of the captured one or more thermal images and/or videos based on a difference between a thermal intensity along one or more blood vessels and a thermal intensity in other regions of the one or more segmented portions;

identifying, by the processing engine, a region of interest comprising the one or more blood vessels in the one or more segmented portions in each frame of the captured one or more thermal images and/or videos;

extracting, by the processing engine, one or more pixel values, representing a set of biosignals, from each frame of the captured one or more thermal images and/or videos based on the identified region of interest;

determining, by the processing engine, one or more parameters associated with vascular function and hemodynamics of the subject based on the extracted one or more pixel values representing the set of biosignals;

comparing, by the processing engine, the determined one or more parameters associated with the vascular function and hemodynamics of the subject with a predetermined set of reference parameters;

evaluating, by the processing engine, the vascular health condition of the subject based on deviation of the determined one or more parameters with respect to the predetermined set of reference parameters on the basis of the comparison, wherein the evaluation of the vascular health condition of the subject considers demographics and medical history of the subject along with the determined one or more parameters; and wherein one or more frames from the captured one or more thermal images and/or videos are rejected when the predefined region is not detected in the one or more frames.

14. The system as claimed in claim 1, wherein the one or more processors are configured to perform contrast stretching on the captured one or more thermal images and/or videos prior to detecting the predefined region.

15. The system as claimed in claim 14, wherein the contrast stretching is optimized to exclude floating-point operations.

* * * * *